(12) United States Patent
Golec et al.

(10) Patent No.: US 6,632,962 B2
(45) Date of Patent: Oct. 14, 2003

(54) CASPASE INHIBITORS AND USES THEREOF

(75) Inventors: Julian M. C. Golec, Swindon (GB); Paul Charifson, Framingham, MA (US); Guy Brenchley, Grove Watage (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 172 days.

(21) Appl. No.: 09/834,052

(22) Filed: Apr. 3, 2001

(65) Prior Publication Data

US 2002/0132833 A1 Sep. 19, 2002

Related U.S. Application Data

(63) Continuation of application No. PCT/US00/21503, filed on Aug. 4, 2000.
(60) Provisional application No. 60/147,706, filed on Aug. 6, 1999.

(51) Int. Cl.[7] ................................................ C07C 61/12
(52) U.S. Cl. .......................................... 562/450; 560/41
(58) Field of Search .......................... 562/450; 560/41; 514/541, 563

(56) References Cited

FOREIGN PATENT DOCUMENTS

| EP | 0 618 223 | 10/1994 |
|---|---|---|
| WO | WO 98/11109 | 3/1998 |
| WO | WO 00/23421 | 4/2000 |
| WO | WO 00/55114 | 9/2000 |
| WO | WO 01/90070 | 11/2001 |
| WO | WO 01/94351 | 12/2001 |

OTHER PUBLICATIONS

A.M.M. Mjalli et al. "Inhibition of Interleukin–1β Converting Enzyme By N–Acyl–Aspartyl Aryloxymethyl Ketones", *Bioorg. Med. Chem. Lett.,* vol. 5, pp. 1409–1414 (1995).
C. Helt et al., "Effects of Caspase Inhibitor Boc–Asp–CH$_2$F on Fetal Ventral Mesencephalic Transplants", *Society for Neuroscience Abstracts,* vol. 24, No. 1–2, p. 1056 (1998); 28th Annual Meeting of the Society for Neuroscience, Part 1, Los Angeles, California, Nov. 7–12, 1998.

*Primary Examiner*—Paul J. Killos
(74) *Attorney, Agent, or Firm*—Lisa A. Dixon; Vertex Pharmaceuticals Incorporated

(57) ABSTRACT

This invention provides novel compounds that are effective as inhibitors of caspase and cellular apoptosis. The invention also provides methods for using the compounds to treat caspase-mediated diseases in mammals. The compounds have the general formula I:

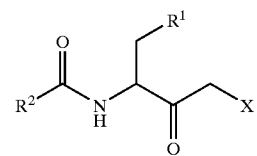

wherein X is F or Cl; $R^1$ is COOH, COO(alkyl), or an isostere thereof; and $R^2$ is an aryl group.

14 Claims, No Drawings

CASPASE INHIBITORS AND USES THEREOF

CROSS-REFERENCE TO RELATED APPLICATIONS

This application is a continuing application of co-pending International Patent Application PCT/US00/21503, filed Aug. 4, 2000, which was published Feb. 15, 2001 under PCT Article 21(2) in English as Publication No. WO 01/10383, which claims the benefit of United States provisional patent application No. 60/147,706, filed Aug. 6, 1999.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283–1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97–R$_{103}$). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-l (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure CH$_3$CO—[P4]—[P3]—[P2]—CH(R)CH$_2$CO$_2$H where P2 to P4 represent an optimal amino acid recognition sequence and R is an aldehyde, nitrile or ketone capable of binding to the caspase cysteine sulfhydryl. Rano and Thornberry, *Chem. Biol.* 4, 149–155 (1997); Mjalli, et al., *Bioorg. Med. Chem. Lett.* 3, 2689–2692 (1993); Nicholson et al., *Nature* 376, 37–43 (1995). Irreversible inhibitors based on the analogous tetrapeptide recognition sequence have been prepared where R is an acyloxymethylketone —COCH$_2$OCOR'. R' is exemplified by an optionally substituted phenyl such as 2,6-dichlorobenzoyloxy and where R is COCH$_2$X where X is a leaving group such as F or Cl. Thornberry et al., *Biochemistry* 33, 3934 (1994); Dolle et al., *J Med. Chem.* 37, 563–564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation*, 97, 276 (1998); Endres et al., *J Cerebral Blood Flow and Metabolism*, 18, 238, (1998); Cheng et al., *J. Clin. Invest.*, 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, smaller peptide inhibitors have been prepared.

WO 99/18781 (Cytovia) describes dipeptide inhibitors of apoptotic cell death having the structure

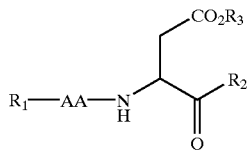

where $R_1$ is an N-terminal protecting group; AA is a residue of any natural α-amino acid, or β-amino acid; $R_2$ is H or $CH_2R_4$ where $R_4$ is an electronegative leaving group, and $R_3$ is alkyl or H, provided that AA is not His, Tyr, Pro or Phe.

Nonpeptide inhibitors of caspase-1 have also been reported. U.S. Pat. No. 5,756,466 (Bemis et al.); Dolle et al., *J. Med. Chem.* 39, 2438 (1996); Dolle et al., *J. Med. Chem.* 40, 1941 (1997).

WO 98/16502 (Warner-Lambert) describes ICE (caspase-1) inhibitors having the structure

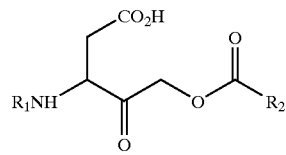

wherein $R_1$ is, inter alia, $R_3CO—$, $R_3$ is, inter alia, $C_1-C_6$ alkyl, aryl, heteroaryl, $—(CHR)_n$-aryl, and $—(CHR)_n$-heteroaryl, and $R_2$ is selected from various groups.

EP623592 (Sterling) describes ICE (caspase-1) inhibitors having the structure

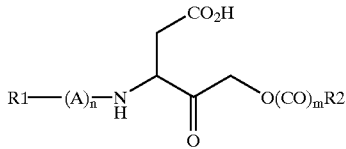

wherein R1 includes aryl and heteroaryl; A is an amino acid; n is 0–4; m is 0 or 1; and $R_2$ is aryl.

WO 97/24339 (Ono) describes ICE (caspase-1) inhibitors having the structure

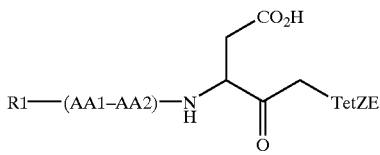

wherein R1 includes aryl and heteroaryl; AA1 and AA2 are single bonds or amino acid residues; Tet represents a tetrazole ring; Z represents alkylene, alkenylene, O, S etc; and E represents H, alkyl, etc.

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are effective as inhibitors of caspases, in particular, caspase-8 and caspase-9 and cellular apoptosis. These compounds have the general formula I:

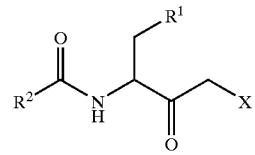

I wherein $R^1$, $R^2$ and X are as described below. $R^2$ is a nonpeptidyl moiety and therefore the present caspase inhibitors are nonpeptidic. Preferred are those compounds where $R^1$ is COOH, $R^2$ is aryl and X is F.

The compounds of this invention are expected to have improved cell penetration and pharmacokinetic properties and, as a consequence of their potency, have improved efficacy against diseases where caspases are implicated.

DETAILED DESCRIPTION OF THE INVENTION

This invention provides novel compounds, and pharmaceutically acceptable derivatives thereof, that are effective as inhibitors of caspases, in particular, caspase-8 and caspase-9 and cellular apoptosis. The invention also provides methods for using the compounds to treat caspase-mediated disease states in mammals. The compounds have the general formula I:

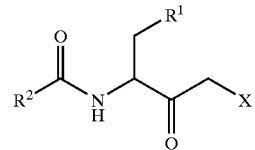

I wherein X is F or Cl;
$R^1$ is COOH, COO(alkyl), or an isostere thereof; and
$R^2$ is an aryl group.

As used herein, unless otherwise indicated, the term "aryl" refers to substituted or unsubstituted monocyclic or bicyclic, five to ten membered ring carbocyclic or heterocyclic aromatic groups, and partially unsaturated analogs thereof. Such groups include, but are not limited to, phenyl, naphthyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, quinazolinyl, quinoxalinyl, 1,8-naphthyridinyl, pteridinyl, tetrazolyl, and chromanyl.

Optional substituents on the aryl ring include, but are not limited to, halo, alkyl, aralkyl, alkoxy, alkoxyaryl, haloalkyl, haloalkoxy, aryl, aryloxy, hydroxy, alkoxycarbonyl, carboxyl, alkylcarbonyl, alkylcarbonylamino, alkylcarbonylalkylamino, alkylamino, alkylaminocarbonyl, dialkylamino, dialkylaminocarbonyl, alkylthio, cyano, and any two adjacent substituents taken together may optionally form a fused, partially unsaturated or fully unsaturated five to seven membered ring containing zero to two heteroatoms.

As used herein, the following definitions shall apply unless otherwise indicated. The term "alkyl" and "alkoxy" used alone or as part of a larger moiety shall include both straight and branched chains containing one to six carbon atoms. The terms "haloalkyl" and "haloalkoxy" means alkyl or alkoxy, as the case may be, substituted with one or more halogen atoms. The term "halogen" means F, Cl, Br, or I. The term "heteroatom" means N, O or S and shall include any oxidized form of nitrogen and sulfur, and the quaternized form of any basic nitrogen.

Isosteres or bioisosteres of carboxylic acids and esters result from the exchange of an atom or group of atoms to create a new compound with similar biological properties to the parent carboxylic acid or ester. The bioisosteric replacement may be physicochemically or topologically based. An example of an isosteric replacement for a carboxylic acid is CONHSO$_2$(alkyl) such as CONHSO$_2$Me.

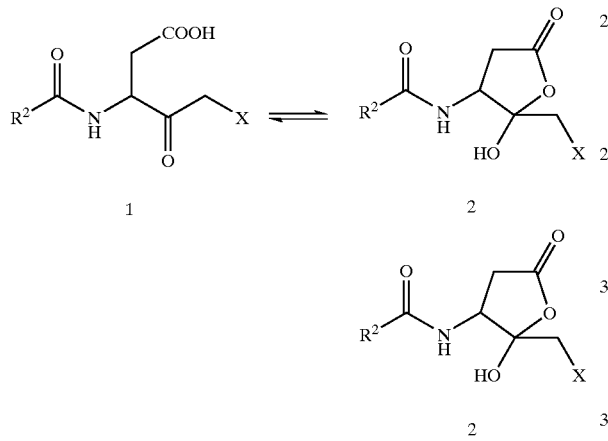

Compounds of this invention where R$^1$ is COOH are gamma ketoacids which may exist in solution as either the open form 1 or the cyclized hemiketal form 2, as shown above. The representation herein of either isomeric form is meant to include the other.

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C- enriched carbon are within the scope of this invention.

Preferred compounds of this invention are those compounds of formula I having one or more, and most preferably all, of the following features: (a) R$^1$ is COOH; (b) R$^2$ is an optionally substituted group selected from phenyl, naphthyl, or a five, six, nine or ten membered heteroaryl having one or two heteroatoms; and/or (c) X is F.

The compounds of this invention may be prepared in general by methods known to those skilled in the art for analogous compounds, as illustrated by the general Scheme I below and by the preparative examples shown below.

Scheme I

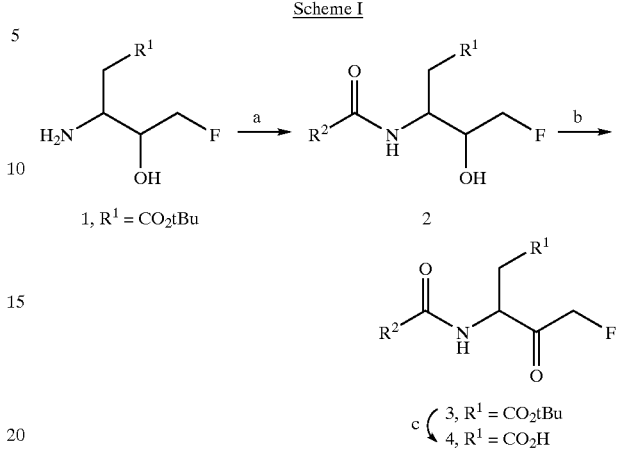

a) R$^2$COOH/EDC/HOBT/DMAP; (b) Dess-Martin; (c) TFA

The starting aminoalcohol 1 may be obtained according to the method of Revesz et al., *Tetrahedron Lett.*, 1994, 35, 9693. Treatment of 1 according to step (a) with an appropriately substituted carboxylic acid, R$^2$COOH, in the presence of 1-(3-dimethylaminopropyl)-3-ethylcarbodiimide hydrochloride, 1-hydroxybenzotriazole and dimethylaminopyridine provides the hydroxyamide 2. Dess-Martin oxidation of 2 (step b) results in the ketoamide 3, which may be de-esterified with TFA (step c) to the desired carboxylic acid 4.

The compounds of this invention are designed to inhibit, either directly or indirectly, caspases that promote apoptosis. Therefore, the compounds of this invention may be assayed for their ability to inhibit caspase activity and apoptosis. Assays for each of the activities are known in the art and are described below in detail in the Testing section.

According to another embodiment, the invention provides a composition comprising a compound of this invention or a pharmaceutically acceptable salt thereof, as described above, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by infection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral", as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to caspase-mediated diseases, such as those associated with abnormally high apoptosis. Such diseases include stroke, traumatic brain injury, spinal cord injury, meningitis, Alzheimers disease, Parkinson's disease, Huntington's disease, Kennedy's disease, prion disease, multiple sclerosis, amyotrophic lateral sclerosis, spinal muscular atrophy, myocardial infarction, congestive heart failure and various other forms of acute and chronic heart disease, atherosclerosis, ageing, burns, organ transplant rejection, graft versus host disease, hepatitis-B, -C, G, various forms of liver disease including acute alcoholic hepatitis, yellow fever, dengue fever, Japanese encephalitis, glomerulonephritis, renal disease, H. pylori-associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves disease, autoimmune gastritis, autoimmune hemolytic anemia, autoimmune neutropenia, thrombocytopenia, HIV-related encephalitis, myasthenia gravis, small bowel inchemia in disease or post surgery, psoriasis, atopic dermatitis, myelodysplatic syndrome, acute and chronic myelogenous leukemia, metastatic melanoma, Kaposi's sarcoma, and Wiscott-Aldrich syndrome. The compounds and compositions are also useful in treating complications associated with coronary artery bypass grafts and as a component of immunotherapy for the treatment of various forms of cancer.

The amount of compound present in the above-described compositions should be sufficient to cause a detectable decrease in the severity of the disease or in caspase activity and/or cell apoptosis, as measured by any of the assays described in the examples.

The compounds of this invention are also useful in methods for preserving cells, such as may be needed for an organ transplant or for preserving blood products. Similar uses for caspase inhibitors have been reported (Schierle et al., *Nature Medicine*, 1999, 5, 97). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

EXAMPLE 1

3-Benzoylamino-5-fluoro-4-oxo-pentanoic Acid

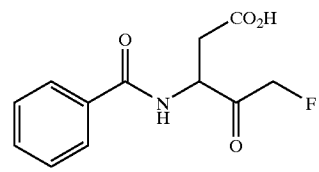

Step A: 3-Benzoylamino-5-fluoro-4-oxo-pentanoic Acid Tert-butyl Ester

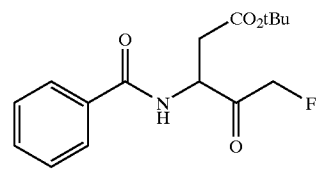

1,1,1-Triacetoxy-1,1-dihydro-1,2-benzodioxol-3(1H)-one (273 mg, 0.64 mmol) was added in one portion to a stirred solution of 3-benzoylamino-5-fluoro-4-hydroxy-pentanoic acid tert-butyl ester (100 mg, 0.32 mmol) (prepared from benzoic acid and 3-amino-5-fluoro-4-hydroxy-pentanoic acid tert-butyl ester using standard coupling procedures eg. HOBT, DMAP, and EDC) in dry dichloromethane (DCM) (2 ml) at 0° C. The mixture was brought to room temperature (r.t.) during 16 h, diluted with EtOAc, then poured into a 1:1 mixture of saturated aqueous sodium hydrogen carbonate and saturated aqueous sodium thiosulphate. The organic layer was removed and the aqueous layer re-extracted with EtOAc. The combined organic organic extracts were dried ($Na_2SO_4$) and concentrated. The residue was purified by flash chromatography (30% EtOAc in hexane) to afford the title compound as a colourless gum (94 mg, 95%): $^1$H NMR ($CDCl_3$) δ 7.80 (2H, m), 7.50 (4H, m), 5.2 (3H, m), 2.95 (2H, m), 1.45 (9H, s); $^{13}$C NMR ($CDCl_3$) δ 203.19, 203.02, 171.02, 167.57, 133.54, 133.04, 132.60, 129.16, 127.97, 127.53, 85.52, 83.70, 82.80, 53.13, 53.03, 36.63, 36.61, 28.44, 28.37; $^{19}$F NMR ($CDCl_3$) δ −232.09(t, J 49 Hz).

Step B: 3-Benzoylamino-5-fluoro-4-oxo-pentanoic Acid

Trifluoroacetic acid (TFA) (10 ml) was added to a stirred ice cold solution of above prepared 3-benzoylamino-5-fluoro-4-oxo-pentanoic acid tert-butyl ester (600 mg, 1.94 mmol) in dry DCM (10 ml). The mixture was stirred at 0° C. for 0.5 h then at r.t. for 0.5 h. The mixture was concentrated under reduced pressure and the residue redissolved in dry DCM. This process was repeated several times in order to remove excess TFA. The resulting gum was triturated with $Et_2O$. Filtration of the resulting suspension yielded the title compound as finely divided white powder (333 mg, 68%): $^1$H NMR (DMSO) δ 12.6 (1H, br s), 8.8 (1H, br m), 7.85 (2H, m), 7.50 (3H, m), 4.90 (2H, m), 4.80 (1H, m), 2.80 (2H, m); $^{13}$C NMR (DMSO) δ 166.97, 133.72, 132.5, 128.70, 127.83, 52.64, 34.58; $^{19}$F NMR (DMSO) δ −226.66 (m), −230.34(m), −232.24(m); Acc. Mass; Calc. 254.0828, Found 254.0793.

EXAMPLE 2

5-Fluoro-3-(3-methyl-benzoylamino)-4-oxo-pentanoic Acid

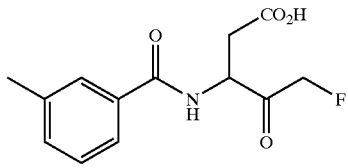

This was prepared using procedures similar to those described in Example 1 to provide an off white foam: IR (Solid) 1739 1668, 1652; $^1$H NMR (DMSO) δ 2.4 (3H, s), 2.6–3.0 (2H, m), 4.4–4.6 (2H, m), 4.7–4.9 (1H, m), 5.2–5.4 (2H, m), 7.3 (2H, m), 7.7–7.9 (2H, m), 8.4–9.0 (1H, m), 12.3–12.8 (1H, br s); $^{13}$C NMR (DMSO) 21.27, 32.86, 34.58, 48.01, 52.55, 83.58, 85.35, 125.00, 125.03, 128.23, 128.33, 128.58, 128.64, 132.47, 132.66, 133.59, 134.03, 137.94, 138.03, 166.80, 167.02, 167.10, 172.14, 173.47, 202.98, 203.13; $^{19}$F NMR (DMSO) δ −226.75(t), −230.5(t), −232.25(t); Acc. Mass; Calc. 268.098511, Found 268.098892.

EXAMPLE 3

5-Fluoro-3-(4-methyl-benzoylamino)-4-oxo-pentanoic Acid

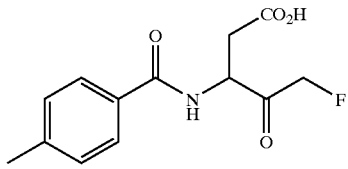

This was prepared using procedures similar to those described in Example 1 to provide an off white foam: IR (Solid) (Solid) 1771, 1739, 1632; $^1$H NMR (DMSO) δ 2.4 (3H, s), 2.6–3.0 (2H, m), 4.4–4.6 (2H, m), 4.8–5.0(1H, m), 5.2–5.4 (2H, m), 7.3 (2H, m), 7.8 (2H, m), 8.4–9.0 (1H, m); $^{13}$C (DMSO) δ 21.34, 32.85, 34.60, 52.50, 83.57, 85.38, 127.83, 127.87, 129.17, 129.23, 130.78, 141.86, 142.09, 166.75, 166.79, 166.85, 172.14, 173.47, 203.03, 203.17, 203.60; $^{19}$F NMR (DMSO) δ −226.75(t), −230.5(t), −232.25 (t); Acc. Mass; Calc. 268.098511, Found 268.098793.

EXAMPLE 4

3-(2-Chlorobenzoylamino)-5-fluoro-4-oxo-pentanoic Acid

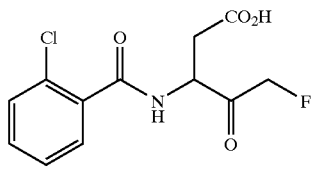

This was prepared using procedures similar to those described in Example 1 to provide a white powder: IR (solid) 3347, 2930, 1744, 1731, 1630, 1541; $^1$H NMR (DMSO) δ 2.64–2.95 (2H, m), 4.47–4.61 (0.7H, m), 4.67–4.89 (1H, m), 5.23–5.44 (1.3H, m), 7.39–7.53 (4H, m), 8.67, 9.00, 9.06 (1H, 3×d, J 8.0, 8.0, 7.0 Hz); $^{13}$C NMR (DMSO) δ 32.69, 34.68, 47.79, 52.42, 53.07, 81.47, 83.56 (d, J 179 Hz), 127.37, 127.47, 129.26, 129.34, 129.98, 130.19, 130.29, 130.35, 131.41, 131.55, 136.06, 136.45, 136.48, 166.66, 166.93, 167.04, 171.99, 173.24, 173.89, 202.40, 202.54; $^{19}$F NMR (DMSO) δ −226.57 (t), −230.40 (t), −232.33 (t); Acc. Mass MH+; Calc. 288.0439, Found 288.0436.

EXAMPLE 5

3-(3-Chlorobenzoylamino)-5-fluoro-4-oxo-pentanoic Acid

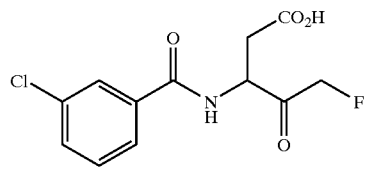

This was prepared using procedures similar to those described in Example 1 to provide a white powder: IR (solid) 3320, 1781, 1742, 1643, 1533; $^1$H NMR (DMSO)δ 2.63–2.95 (2H, m), 4.43–4.60 (0.7H, m), 4.74–4.93 (1H, m), 5.21–5.39 (1.3H, m), 7.51–7.55 (1H, m), 7.66–7.81 (1H, m), 7.81–7.96 (2H, m), 8.69, 8.94, 9.05 (1H, 3×d, J 8.0, 8.0, 7.0Hz); $^{13}$C NMR (DMSO) δ 33.35, 34.98, 35.11, 48.75, 53.09, 53.70, 81.91, 82.38, 84.10 (d, J 179Hz), 127.21, 128.13, 131.24, 131.29, 132.26, 132.43, 134.01, 134.06, 136.10, 136.53, 136.59, 165.84, 166.03, 166.11, 172.55, 173.85, 174.91, 203.30, 203.45.

EXAMPLE 6

3-(4-Chlorobenzoylamino)-5-fluoro-4-oxo-pentanoic Acid

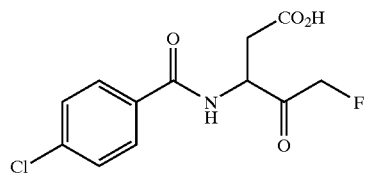

This was prepared using procedures similar to those described in Example 1 to provide a white powder: IR (solid) 3299, 1774, 1735, 1637, 1596, 1534, 1487; $^1$H NMR (DMSO) δ 2.57–2.95 (2H, m), 4.40–4.59 (0.7H, m), 4.73–4.92 (1H, m), 5.17–5.38 (1.3H, m), 7.55–7.62 (2H, m), 7.86–7.96 (2H, m), 8.63, 8.90, 9.01 (1H, 3 × d, J 8,8,7 Hz); $^{13}$C NMR (DMSO) δ 33.33, 35.01, 48.66, 53.06, 53.65, 81.90 (d, J 176 Hz), 82.34 (d, J 178 Hz), 84.11 (d, J 178 Hz), 129.28, 129.35, 130.29, 130.31, 132.83, 133.25, 133.36, 137.26, 137.45, 166.24, 166.37, 166.46, 172.59, 173.9, 174.94, 203.40, 203.54.

EXAMPLE 7

3-(3,4-Dichlorobenzoylamino)-5-fluoro-4-oxo-pentanoic Acid

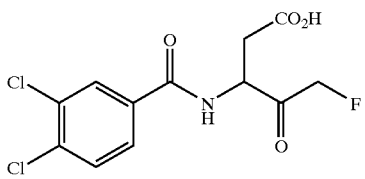

This was prepared using procedures similar to those described in Example 1 to provide a colorless powder: IR (solid) 2981, 1708, 1638, 1538, 1033; $^1$H (CD$_3$OD) δ 2.66–3.28 (2H, m), 4.41–5.35 (5H, m), 7.57–8.01 (3H, m); $^{13}$C (CD$_3$OD) δ 33.0, 33.7, 33.8, 34.2, 48.7, 51.3, 52.9, 52.9, 80.7 (d, J 176.8), 81.6 (d, J 177.1 Hz), 82.4 (d, J 178.5 Hz), 84.5 (d, J 181.6 Hz), 127.3, 129.8, 130.8, 130.9, 132.6, 132.7, 132.8, 133.8, 134.2, 134.9, 135.0, 135.6, 135.7, 136.0, 136.2, 166.7, 166.8, 166.9, 167.2, 172.9, 174.0, 174.4, 174.5, 203.1 (d, J 15.7 Hz).

EXAMPLE 8

3-(3,5-Dichlorobenzoylamino)-5-fluoro-4-oxo-pentanoic Acid

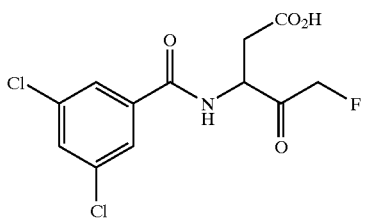

This was prepared using procedures similar to those described in Example 1 to provide a colorless powder: IR (solid) 3302, 1747, 1706, 1647, 1523; $^1$H NMR (DMSO) δ: 2.65–2.98 (2H, m), 4.42–4.54 (0.6H, m), 4.74–4.94 (1H, m), 5.17–5.40 (1.4H, m), 7.83–7.96 (3H, m), 8.85, 9.05, 9.17 (1H, 3d), 12.39 (1H, br s); MS (FAB+ve, HR) Calculated for C$_{12}$H$_{10}$Cl$_2$FNO$_4$ (MH+) 322.0049, found 322.0044.

EXAMPLE 9

5-Fluoro-3-(2-fluorobenzoylamino)-4-oxo-pentanoic Acid

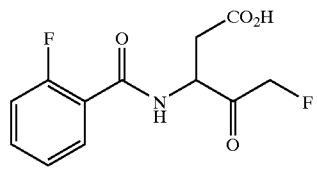

This was prepared using procedures similar to those described in Example 1 to provide an off white foam: IR (solid) 3204, 1785, 1645, 1612, 1530; $^1$H (DMSO) δ 2.68–3.25 (2H, m), 4.45–4.57 (0.6H, bd), 4.83–4.90 (1H, s), 5.24–5.36 (1.4H, m), 7.29–7.34 (2H, m), 7.54–7.59 (1H, m), 7.64–7.67 (1H, m), 7.96, 8.38, 8.83 (1H, 3×br s); $^{13}$C (DMSO) δ 39.76, 53.17, 85.78 (d), 117.17 (d), 123.7, 125.42 (d), 131.08, 133.82 (d), 158.91(d), 164.85, 172.60, 203.07; MS (FAB+ve, HR) Calculated for C$_{12}$H$_{12}$F$_2$NO$_4$ (MH+) 272.0734, found 272.0730.

EXAMPLE 10

5-Fluoro-3-(3-fluorobenzoylamino)-4-oxo-pentanoic Acid

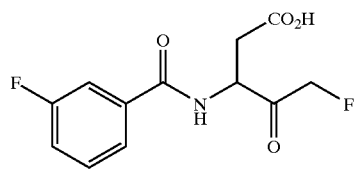

This was prepared using procedures similar to those described in Example 1 to provide a colorless glass: IR (solid) 3315, 1785, 1740, 1645, 1587, 1352; $^1$H (DMSO) δ 2.58–2.99 (2H, m), 4.45–4.57 (0.7H, m), 4.74–4.93 (1H, s), 5.18–5.75 (1.3H, m), 7.41–7.88 (4H, m), 8.64, 8.93, 9.02 (1H, 3×d, J 8, 8, 7 Hz); $^{13}$C (DMSO) δ 32.84, 34.48, 34.61, 43.75, 52.08, 53.19, 81.39, 83.59, 85.37 (d, J 175 Hz), 135.83, 135.88, 135.95, 136.33, 136.40, 136.48, 161.06 (d, J 240), 165.48, 165.61, 166.78, 171.03, 172.04, 173.35, 174.40, 202.50, 202.65, 202.96, 202.81; MS (FAB+ve, HR) Calculated for C$_{12}$H$_{12}$F$_2$NO$_4$ (MH+) 272.0734, found 272.0730.

EXAMPLE 11

5-Fluoro-3-(4-fluorobenzoylamino)-4-oxo-pentanoic Acid

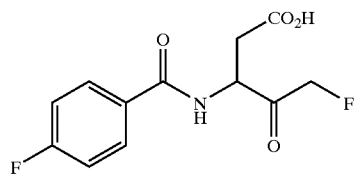

This was prepared using procedures similar to those described in Example 1 to provide a white powder: IR (solid) 3387, 3073, 1773, 1633, 1602, 1539, 1503; $^1$H (DMSO) δ 2.68–2.96 (2H, m), 4.44–4.57 (0.7H, m), 4.79–4.90 (1H, m), 5.17–5.38 (1.3H, m), 7.31–7.35 (2H, m), 7.82–7.99 (1H, m), 8.56, 8.85, 8.98 (1H, 3 x d, J 8.0, 8.0, 7.0 Hz); $^{13}$C (DMSO) δ 33.36, 34.17, 35.16, 48.61, 52.99, 53.66, 81.93, 82.35, 84.10 (d), 116.03 (d), 116.10 (d), 130.58, 130.61, 130.99, 131.05, 131.08, 131.14, 163.69 (d), 163.79 (d), 166.27, 166.45, 172.58, 173.91, 174.94, 203.43, 203.58; MS (FAB+ve, HR) Calculated for C$_{12}$H$_{12}$F$_2$NO$_4$ (MH+) 272.0734, found 272.0743.

EXAMPLE 12

5-Fluoro-4-oxo-3-(3-trifluoromethylbenzoylamino)-pentanoic Acid

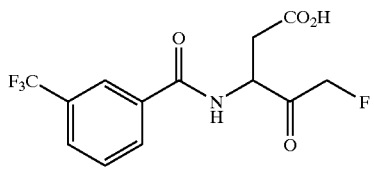

This was prepared using procedures similar to those described in Example 1 to provide a colorless powder: IR (solid) 1741, 1712, 1644; $^1$H (DMSO) δ 2.6–3.0(2H, m), 4.4–4.6(2H, m), 4.7–5.0(1H, m), 5.2–5.4(2H, m), 7.7(1H, m), 8.0(1H, m), 8.1–8.3(2H, m), 8.8–9.3(1H, m); $^{13}$C (DMSO) δ 31.72, 33.30, 33.45, 52.13, 54.09, 80.25, 80.72, 82.00, 82.46, 84.24, 112.08, 121.79, 123.11, 123.15, 124.50, 127.21, 127.33, 127.89, 128.15, 128.21, 128.47, 128.53, 128.79, 133.34, 133.76, 133.83, 157.31, 157.68, 164.19, 164.36, 164.42, 170.90, 172.17, 173.30, 201.61, 201.75.

EXAMPLE 13

5-Fluoro-3-(4-trifluoromethylbenzoylamino)-4-oxo-pentanoic Acid

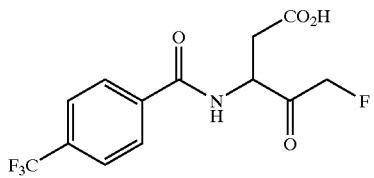

This was prepared using procedures similar to those described in Example 1 to provide a powder: IR (solid) 1772.3, 1739.6, 1644.1; $^1$H (DMSO) δ 2.6–3.0(2H, m), 4.4–4.6(2H, m), 4.7–5.0(1H, m), 5.2–5.4(2H, m), 7.8(2H, m), 8.1(2H, m), 8.8–9.2(1H, m); $^{13}$C (DMSO) δ 32.88, 34.50, 34.62, 48.29, 52.64, 53.26, 81.40, 81.88, 83.15, 83.62, 85.40, 122.91, 125.62, 125.73, 125.77, 125.81, 128.77, 128.81, 131.45, 131.62, 131.77, 131.94, 132.08, 137.42, 137.84, 165.68, 165.83, 165.89, 172.05, 173.35, 174.37, 202.77, 202.92.

EXAMPLE 14

3-(Biphenyl-3-carboxamido)-5-fluoro-4-oxo-pentanoic Acid

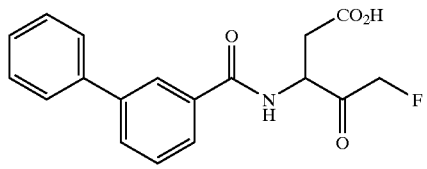

This was prepared using procedures similar to those described in Example 1 to provide a colourless powder: IR (solid) 1778.0, 1745.7, 1639.7; $^1$H NMR (DMSO) δ 2.6–3.0 (2H, m), 4.4–4.6 (2H, m), 4.8–5.0 (1H, m), 5.2–5.5 (2H, m), 7.4–8.0 (8H, m), 8.1–8.2 (1H, m), 8.6–9.2 (1H, m) $^{13}$C NMR (DMSO) δ 32.93, 34.60, 52.60, 53.23, 81.49, 81.89, 83.24, 83.60, 83.65, 85.38, 125.94, 125.97, 126.01, 128.21, 129.40, 129.72, 129.77, 130.10, 130.27, 134.27, 134.72, 134.81, 139.80, 139.86, 140.61, 140.67, 166.73, 166.85, 166.91, 172.12, 173.40, 174.47, 202.91, 203.05; MS (FAB+ve, HR) Calculated for $C_{18}H_{16}FNO_4$ (MH+) 330.114161, found 330.113907.

EXAMPLE 15

3-(Biphenyl-4-carboxamido)-5-fluoro-4-oxo-pentanoic Acid

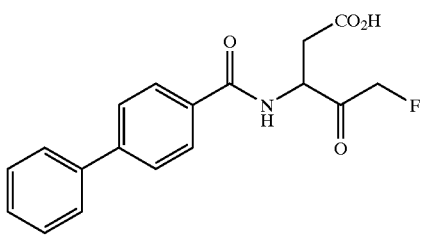

This was prepared using procedures similar to those described in Example 1 to provide a colourless solid: IR (solid) 3292, 1744, 1702, 1643, 1533; $^1$H NMR (DMSO) δ 2.66–3.05 (2H, m), 4.473–4.59 (0.6H, m), 4.80–4.97 (1H, m), 5.19–5.40 (1.4H, m), 7.40–8.01 (9H, m), 8.61, 8.92, 9.02 (1H, 3d), 12.49 (1H, br s); $^{13}$C NMR (DMSO) δ 32.9, 34.6, 48.1, 52.6, 82.5, 84.5 (d, J 178.6 Hz), 126.9, 126.9, 127.3, 128.5, 128.6, 129.4, 132.4, 132.8, 139.4, 139.5, 143.4, 143.5, 166.6, 172.2, 173.5, 203.1 (J 14.4 Hz).

EXAMPLE 16

5-Fluoro-3-(3-methoxybenzoylamino)-4-oxo-pentanoic Acid

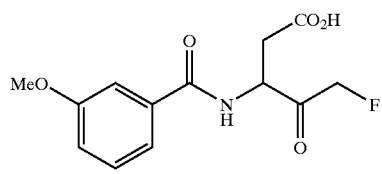

This was prepared using procedures similar to those described in Example 1 to provide an off white foam: IR (solid) 2923, 2848, 1793, 1737, 1650, 1542, 1040; $^1$H (DMSO) δ 2.60–3.05 (2H, m), 3.80 (3H, s), 4.35–4.58 (0.66H, m), 4.73–4.90 (1H, m), 5.16–5.37 (1.33H, m), 7.10–7.18 (1H, m,), 7.37–7.55 (3H, m), 8.51, 8.81, 8.93 (1H, 3d, J 8.0, 8.2, 7.1 Hz); $^{13}$C (DMSO) δ_32.83, 34.54, 52.56, 55.68, 83.57, 85.34, 113.03, 117.72, 117.93, 120.06, 129.82, 129.89, 134.96, 135.44, 159.54, 166.71, 172.103, 202.91, 203.05.

EXAMPLE 17

5-Fluoro-3-(4-methoxy-benzoylamino)-4-oxo-pentanoic Acid

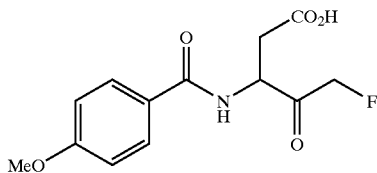

This was prepared using procedures similar to those described in Example 1 to provide a colourless powder: IR (solid) 3271, 1786, 1734, 1640, 1607, 1503, 1261, 1176; $^1$H NMR (DMSO) δ 2.60–3.05 (2H, m), 3.80 (3H, s), 4.35–4.58 (0.66H, m), 4.73–4.92 (1H, m), 5.16–5.37 (1.33, m), 7.02 (2H, d, J 8.9 Hz), 7.82–7.90 (2H, m), 8.34, 8.67, 8.78 (1H, 3d, J 8.0, 8.4, 7.0 Hz); $^{13}$C NMR (DMSO) δ 34.69, 52.55, 113.92, 129.74, 162.31, 167.71.

EXAMPLE 18

2-(3-Acetylaminobenzoylamino)-4-fluoro-3-oxo-butyric Acid

This was prepared using procedures similar to those described in Example 1 to provide an off white powder: IR (solid) 3267, 1747, 1718, 1642, 1598, 1537; $^1$H NMR (DMSO) δ 2.06 (3H, s), 2.65 (1H, dd, J 16.8, 7.3 Hz), 2.89 (1H, dd, J 16.8, 6.1 Hz), 4.50 (m, J 46.9 Hz), 4.83, 4.87 (1H, 2m), 5.27 (m), 7.38–8.01 (5H, m), 8.47, 8.90 (1H, 2d, J 8.0, 7.1 Hz), 10.10 (1H, s); $^{13}$C NMR (DMSO) δ 24.8, 35.1, 53.1, 84.9 (d, J 178.8 Hz), 119.3, 122.6, 123.0, 129.5, 134.8, 140.3, 167.5, 169.4, 172.6, 203.5 (d, J 14.2 Hz); Calculated for $C_{14}H_{15}FN_2O_5$ (MH+) 311.1043, found 311.1038.

EXAMPLE 19

3-(3-Cyanobenzoylamino)-5-fluoro-4-oxo-pentanoic Acid

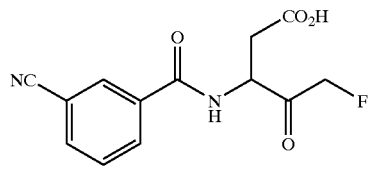

This was prepared using procedures similar to those described in Example 1 to provide a white foam: IR (solid) 3360, 3119, 2935, 1747, 1706, 1639, 1537, 1189; $^1$H NMR (DMSO) δ 2.58–3.02 (2H, m), 4.40–4.65 (0.66H, m), 4.73–4.95 (1H, m), 5.17–5.42 (1.33H, m), 7.66–8.33 (4H, m), 8.80, 9.03, 9.14 (3d, J 8.1, 8.6, 7.2 Hz), 12.52 (brs, 1H); $^{13}$C NMR (DMSO) δ 32.92, 34.46, 52.57, 83.63, 85.40, 111.86, 118.64, 130.23, 131.45, 132.71, 132.71, 134.62, 135.36, 135.51, 165.21, 172.02, 173.29, 202.73, 202.89.

EXAMPLE 20

3-(4-Cyano benzoylamino)-5-fluoro-4-oxo-pentanoic Acid

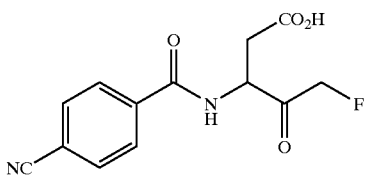

This was prepared using procedures similar to those described in Example 1 to provide a white powder: IR (solid) 3093, 2238 (CN), 1778, 1650, 1537, 1265, 1184, 1055; $^1$H (DMSO) δ 2.58–2.90 (2H, m), 4.40–4.60 (0.66H, m), 4.80–4.95 (1H, m,), 5.17–5.41 (1.33H, m), 7.93–8.05 (4H, m), 8.84, 9.09, 9.19 (3d, J 8.1, 8.6, 7.2 Hz), 12.45 (1H, brs); $^{13}$C (DMSO) δ 32.86, 34.44, 52.62, 56.36, 83.60, 85.38, 114.39, 118.62, 128.68, 132.81, 137.60, 138.02, 165.67, 171.99, 173.29, 202.69, 202.83.

EXAMPLE 21

5-Fluoro-3-(3-iodo-benzoylamino)-4-oxo-pentanoic Acid

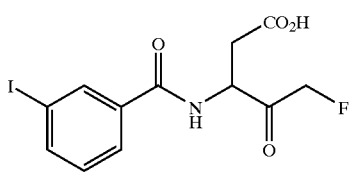

This was prepared using procedures similar to those described in Example 1 to provide a colourless powder: IR (solid) 1635.3, 1708.9, 1741.9; $^1$H NMR (DMSO) δ 2.6–3.0 (2H, m), 4.4–4.6 (2H, m), 4.7–5.0 (1H, m), 5.2–5.4 (2H, m), 7.3 (1H, m), 7.8–8.0 (2H, m), 8.2 (1H, m), 8.6–9.0 (1H, m), 12.4–12.5(1H, br s); $^{13}$C NMR (DMSO) δ 32.86, 34.49, 34.60, 48.22, 52.58, 53.22, 81.41, 81.89, 83.15, 83.58, 83.65, 85.35, 94.96, 127.39, 130.91, 135.65, 136.02, 136.08, 140.42, 140.59, 165.29, 165.44, 165.52, 172.02, 173.32, 174.39, 202.78, 202.92.

EXAMPLE 22

5-Fluoro-3-(naphthyl-1-carboxamido)-4-oxo-pentanoic acid

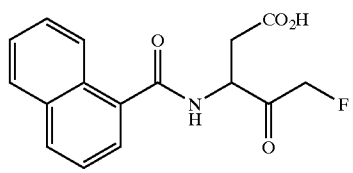

This was prepared using procedures similar to those described in Example 1 to provide a colourless solid: IR (solid) 3252, 1752, 1706, 1650, 1511, 1322; $^1$H NMR (DMSO) δ 2.58–3.05 (2H, m), 4.50–4.79 (0.6H, m), 4.80–5.05 (1H, m), 5.26–5.5.55 (1.33H, m), 7.48–8.7.72 (4H, m), 7.90–8.30 (3H, m), 8.78, 9.10 (2d, J 7.7, and 7.0 Hz), 12.56 (1H, brs); $^{13}$C NMR (DMSO) δ 30.97, 32.84, 48.08, 53.08, 83.22, 85.42, 125.25, 125.60, 125.75, 125.89, 125.96, 126.60, 126.65, 127.10, 127.17, 127.22, 128.58, 130.05, 130.48, 130.60, 133.46, 133.82, 134.09, 134.31, 168.85, 169.23, 172.09, 173.35, 174.16, 202.95, 203.10.

EXAMPLE 23

5-Fluoro-3-(naphthyl-2-carboxamido)-4-oxo-pentanoic Acid

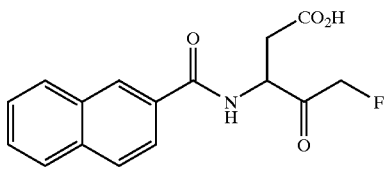

This was prepared using procedures similar to those described in Example 1 to provide a compound having: $^1$H NMR (DMSO) δ 2.60–3.10 (m, 2H), 4.44–4.68 (m, 0.66H), 4.80–5.01 (m, 1H), 5.17–5.42 (m, 1.33H), 7.59–8.18 (m, 6H), 8.45–8.53 (m, 1H), 8.71, 9.02, 9.11 (3d, J 8.1, 8.4, 7.1Hz), 12.52 (brs, 1H); $^{13}$C NMR (DMSO) δ 34.68, 52.67, 83.64, _85.42, 124.63, 127.25, 128.04, 128.15, 128.32, 128.36, 1129.25, 132.42, 134.72, 167.09, 172.14.

EXAMPLE 24

5-Fluoro-4-oxo-3-(pyridyl-4-carboxamido)-pentanoic Acid Trifluoroacetate Salt

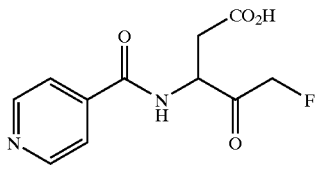

This was prepared using procedures similar to those described in Example 1 to provide a colourless solid: IR (Solid) 1739, 1731, 1715, 1667; $^1$H NMR (DMSO) δ 2.6–3.0(2H, m), 4.4–4.6(2H, m), 4.8–5.0(1H, m), 5.2–5.4 (2H, m), 7.9(2H, m), 8.8(2H, m), 9.0–9.4(1H, m); $^{13}$C NMR (DMSO) δ 33.35, 34.89, 35.05, 48.81, 53.06, 53.74, 82.33, 83.59, 84.12, 85.90, 122.80, 142.22, 142.72, 150.02, 150.16, 165.48, 165.59, 165.68, 172.49, 172.76, 203.07, 203.21.

EXAMPLE 25

5-Fluoro-4-oxo-3-(pyridyl-3-carboxamido)-pentanoic Acid Trifluoroacetate Salt

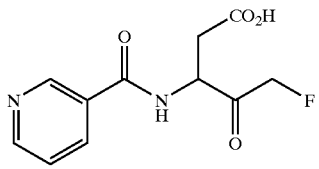

This was prepared using procedures similar to those described in Example 1 to provide a colourless powder: IR (Solid) 1780, 1739, 1667; $^1$H NMR (DMSO) δ 2.6–3.0(2H, m), 4.4–4.6(2H, m), 4.8–5.0(1H, m), 5.2–5.4(2H, m), 7.6 (1H, m), 8.3(1H, m), 8.8(1H, m), 8.9(1H, m), 9.1(1H, m), 9.3(1H, m); $^{13}$C NMR (DMSO) δ 33.45, 35.05, 35.14, 53.03, 53.70, 81.94, 82.35, 83.68, 84.11, 85.89, 124.75, 130.14, 130.51, 137.12, 137.19, 148.63, 148.72, 152.06, 152.13, 152.30, 165.61, 165.73, 172.50, 173.75, 203.19, 203.33; MS (HR) calculated for $C_{11}H_{12}N_2O_4F$ 255.078110, found 255.078003.

EXAMPLE 26

5-Fluoro-3-(furyl-3-carboxamido)-4-oxo-pentanoic Acid

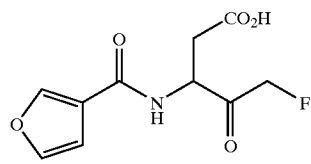

This was prepared using procedures similar to those described in Example 1 to provide an off-white solid: IR (Solid) 1779, 1742, 1639; $^1$H NMR (DMSO) δ 2.6–3.0(2H, m), 4.4–4.6(2H, m), 4.7–5.0(1H, m), 5.2–5.4(2H, m), 6.9 (1H, m), 7.8(1H, m), 8.3(1H, m), 8.5–8.7(1H, m); $^{13}$C NMR (DMSO) δ 32.86, 34.63, 34.71, 47.51, 51.90, 52.58, 81.41, 81.65, 83.15, 83.41, 83.56, 85.34, 103.35, 109.30, 122.05, 122.45, 122.48, 144.49, 144.58, 145.98, 146.03, 146.21, 161.99, 162.21, 162.30, 172.09, 173.35, 174.47, 202.91, 203.05.

EXAMPLE 27

5-Fluoro-3-(1-methyl-1H-pyrrolyl-2-carboxamido)-4-ox o-pentanoic Acid

This was prepared using procedures similar to those described in Example 1 to provide an off-white glass: IR (solid) 2941, 1780, 1739, 1631, 1539; $^1$H NMR (DMSO) δ 2.56–2.77 (1H, m), 2.85–2.96 (1H, m), 3.82 (3H, s), 4.41–4.5.10 (2H, m), 5.17–5.22 (0.5H, m), 5.25–5.30 (0.5H, m), 6.03 (1H, s), 6.84 (1H, s), 6.94–6.96 (1H, m), 7.93, 8.29, 8.39 (1H, 3×d, J 8.0, 8.0, and 7.0 Hz); $^{13}$C NMR (DMSO) δ 32.85, 34.73, 35.01, 36.49, 36.57, 47.23, 51.99, 52.45, 79.90(d, J 171 Hz), 81.69 (d, J 177 Hz), 83.50 (d, J 178 Hz), 107.09, 107.21, 108.39, 113.38, 113.76, 116.36, 124.66, 125.09, 128.62, 128.88, 130.46, 161.67, 172.20, 173.48, 174.51, 203.11, 203.25.

EXAMPLE 28

5-Fluoro-4-oxo-3-(thienyl-2-carboxamido)-pentanoic Acid

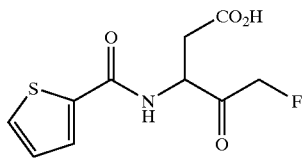

This was prepared using procedures similar to those described in Example 1 to provide a colorless solid: IR (solid) 1777, 1742, 1629; $^1$H NMR (DMSO) δ 2.6–3.0(2H, m), 4.4–4.6(2H, d), 4.8–4.9(1H, m), 5.2–5.4(2H, d), 7.2(1H, m), 7.8–8.0(2H, m), 8.5–9.0(1H, m), 12–13.5(1H, br s); $^{13}$C NMR (DMSO) δ 32.83, 34.58, 34.68, 52.31, 53.02, 81.36, 81.71, 83.11, 83.47, 83.55, 85.32, 128.28, 128.33, 128.38, 129.20, 129.54, 131.77, 132.03, 138.74, 139.26, 139.37, 161.44, 161.68, 161.73, 172.04, 173.31, 174.41, 202.81, 202.95; MS (HR) calculated for $C_{10}H_{11}NO_4FS$ 260.039283, found 260.039177.

EXAMPLE 29

5-Fluoro-4-oxo-3-(thienyl-3-carboxamido)-pentanoic Acid

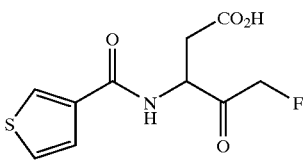

This was prepared was prepared using procedures similar to those described in Example 1 to provide a colorless solid: IR (Solid) 1774, 1626; $^1$H NMR (DMSO) δ 2.6–3.0(2H, m), 4.4–4.6(2H, d), 4.7–4.9(1H, m), 5.2–5.4(2H, d), 7.5–7.7(2H, m), 8.2(1H, m), 8.4–8.8(1H, m), 11.5–13.5(1H, br s); $^{13}$C NMR (DMSO) δ 32.84, 34.60, 34.70, 52.20, 52.83, 81.43, 81.73, 83.17, 83.49, 83.56, 85.33, 127.02, 127.22, 127.26, 127.29, 127.34, 129.80, 130.14, 136.76, 137.26, 162.37, 162.55, 162.61, 172.10, 173.39, 174.49, 202.93, 203.07, 203.59, 204.52; MS (HR) calculated for $C_{10}H_{11}NO_4FS$ 260.039283, found 260.039124.

EXAMPLE 30

5-Fluoro-4-oxo-3-(thiazolyl-2-carboxamido)-pentanoic Acid

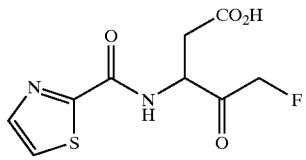

This was prepared using procedures similar to those described in Example 1 to provide an off-white gum: IR (semi-solid) 1792, 1744, 1660; $^1$H NMR (DMSO) δ 2.6–3.2 (2H, m), 4.4–4.6(2H, m), 4.7–5.0(1H, m), 5.2–5.5(2H, m), 7.9–8.1(2H, m), 8.7–9.5(1H, m); 13C NMR (DMSO) δ 33.05, 34.51, 34.62, 47.85, 52.56, 53.17, 81.62, 83.37, 83.47, 85.28, 126.51, 126.75, 144.31, 144.36, 144.41, 159.57, 159.65, 62.86, 163.08, 172.15, 173.21, 202.23, 202.38.

EXAMPLE 31

5-Fluoro-3-(1H-indolyl-2-carboxamido)-4-oxo-pentanoic Acid

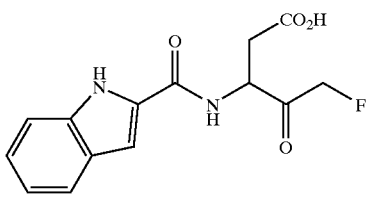

This was prepared using procedures similar to those described in Example 1 to provide a colorless solid: IR (solid) 3363, 1790, 1598, 1580, 1534, 1457, 1432, 1204, 1149, 1066, 1050, 750; $^1$H NMR (DMSO) δ 8.40, 7.85 (1H, 2×m), 8.15 (2H, m); 7.4 (1H, m), 7.15 (2H, m), 5.25, 4.50(2H, 2×m), 5.0, 4.80 (1H, 2×m), 3.32, 2.90, 2.68(2H, 3×m) $^{13}$C NMR (DMSO) δ 202.04, 201.90, 170.85, 163.59, 134.95, 127.62, 124.88, 120.91, 119.73, 119.46, 110.78, 108.13, 83.87, 82.09, 50.45, 33.45.

EXAMPLE 32

3-(3-Carboxybenzoylamino)-5-fluoro-4-oxo-pentanoic Acid

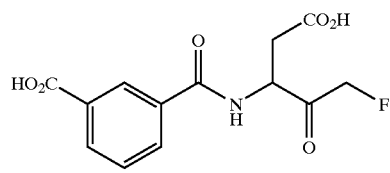

This was prepared using procedures similar to those described in Example 1 to provide a fluffy white solid: IR (solid) 1642, 1707; $^1$H NMR (DMSO) δ 2.6–3.1 (2H, m), 4.4–4.6 (0.7H, m), 4.8–5.0 (1H, m), 5.2–5.4 (1.4H, m), 7.6 (1H, m), 8.1–8.2 (2H, m), 8.5–8.6(1H, m), 8.7–9.2 (1H, m); $^{13}$C NMR (DMSO) δ 32.84, 34.52, 34.61($CH_2$), 52.62, 53.23(CH), 81.40, 81.92, 83.15, 83.57, 83.67, 85.35 ($CH_2F$), 128.43, 128.50, 129.13 (ArCH), 131.32, 131.38 (ArC), 132.09, 132.52, 132.68 (ArCH), 134.00, 134.44, 134.49 (ArC), 166.00, 166.16, 166.21, 167.13, 167.17, 167.19, 172.06, 173.38, 174.42, 202.85, 202.99 (CO).

EXAMPLE 33

3-(4-Methylamidobenzoylamino)-5-fluoro-4-oxo-pentanoic Acid

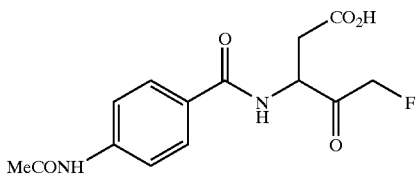

This was prepared using procedures similar to those described in Example 1 to provide a brown powder: IR (solid) 3267, 1747, 1717, 1641, 1597, 1537, 1395; $^1$H NMR (DMSO) δ 2.07 (3H, s), 2.65 (1H, dd, J 16.8 and 7.3 Hz), 2.89 (1H, dd, J 16.8 and 6.1 Hz), 4.49 (2H, m, J 46.1 Hz, minor isomer), 4.79 and 4.89 (1H, 2m), 5.25/5.26 (2H, 2dd, J 46.6 and 18.0/46.8 and 16.7 Hz, major isomer), 7.67 (2H, d, J 8.7 Hz), 7.82 (2H, d, J 8.8 Hz), 7.84 (1H, d, J 8.8 Hz), 8.38/8.81 (1H, 2d, J 8.1/7.1 Hz), 10.18/10.19 (1H, 2s); $^{13}$C NMR (DMSO) δ 25.0 (CH$_3$), 35.1 (CH$_2$), 53.0 (CH), 85.0 (d, J 178.7 Hz, CH$_2$F), 118.9 (ArCH×2), 122.6 (ArCH), 128.3 (ArC), 129.3 (ArCH×2), 143.3 (ArC), 167.0 (CO), 169.6 (CO), 172.7 (CO), 203.6 (d, J 14.6 Hz, CO).

EXAMPLE 34

5-Fluoro-3-(5-phenyl-furyl-2-carboxamido)-4-oxo-pentanoic Acid

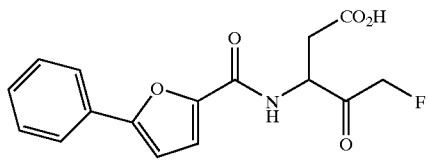

This was prepared using procedures similar to those described in Example 1 to provide a white foam: IR (solid) 1786, 1736, 1637, 1593, 1543, 1477; $^1$H NMR (DMSO) δ 2.60–3.00 (2H, m), 4.80–4.99 (1H, m), 5.09–5.44 (2H, m), 7.18 (1H, d, J 3.6 Hz), 7.26 (1H, d, J 3.5 Hz), 7.56 (2H, d, J 8.5 Hz), 7.94 (2H, d, J 8.5 Hz), 8.78–9.02 (1H, m); $^{13}$C NMR (DMSO) δ 31.39, 33.21 (CH$_2$), 50.60, 51.14 (CH), 82.04, 83.82 (CH$_2$), 104.47, 115.39, 115.51 (ArCH), 124.99 (ArCH), 126.97, 127.02 (ArC), 127.89 (ArCH), 132.07, 132.11 (ArC), 145.13, 145.46 (ArC), 152.57, 152.70 (ArC), 156.33, 156.47 (CO), 170.65, 171.87 (CO), 201.89, 201.33 (CO).

EXAMPLE 35

3-(3-Benzyloxybenzoylamino)-5-fluoro-4-oxo-pentanoic Acid

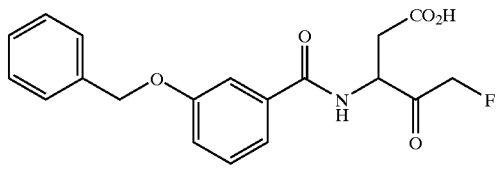

This was prepared using procedures similar to those described in Example 1 to give a white foam: IR (solid) 3327, 1786, 1743, 1641, 1581, 1531, 1481, 1292, 1227, 1049; $^1$H NMR (DMSO) δ 2.66 (1H, dd, J 16.8, 7.4 Hz), 2.83–3.01 (1H, m), 4.39–4.59 (0.66H, m), 4.72–4.95 (1H, m), 5.16 (2H, s), 5.18–5.40 (1.33H, m), 7.13–7.59 (9H, m), 8.53, 8.82, 8.94 (1H, 3×d, J 8.1, 8.5, 7.1 Hz); $^{13}$C NMR (DMSO) δ 32.82, 34.53 (CH$_2$), 48.06, 52.56, 53.11 (CH), 69.76 (CH$_2$), 81.82, 83.57, 85.34 (CH$_2$), 104.23, 104.42 (ArC), 114.11, 118.30, 120.31 (ArCH), 128.10, 128.27, 128.81, 129.85, 129.93 (ArCH), 134.95, 135.42, 137.13 (ArC), 166.42, 166.56, 166.63, 172.11, 173.44 (CO), 202.94, 203.08 (CO).

EXAMPLE 36

3-(3-(2-Phenylethoxy)benzoylamino)-5-fluoro-4-oxo-pentanoic Acid

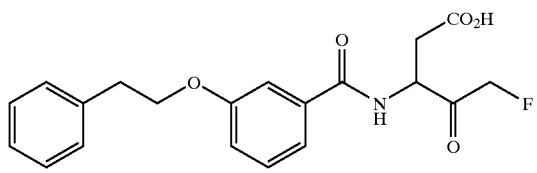

This was prepared using procedures similar to those described in Example 1 to give a white foam: IR (solid) 1793, 1742, 1634, 1583, 1527, 1291, 1235; 1194, 1055, 927; $^1$H NMR (DMSO) δ 2.66 (1H, dd, J 16.8, 7.4 Hz), 2.83–3.01 (1H, m), 3.06 (2H, t, J 6.8 Hz), 4.25 (2H, t, J 6.8 Hz), 4.39–4.59 (0.66H, m), 4.72–4.95 (1H, m), 5.18–5.40 (1.33H, m), 7.09–7.52 (9H, m), 8.52, 8.80, 8.93 (1H, 3×d, J 8.1, 8.5, 7.0 Hz); $^{13}$C NMR (DMSO) δ 31.32, 33.05, 33.78 (2×CH$_2$), 46.56, 51.09, 51.66 (CH), 67.22 (CH$_2$), 82.09, 83.87 (CH$_2$), 112.10, 116.57, 116.80, 118.75, 125.20, 127.22, 127.85, 128.38, 128.45 (ArCH), 133.44, 133.92, 133.99, 137.16 (ArC), 164.99, 165.13, 165.19, 170.66, 171.96, 173.02 (CO), 201.45, 201.59 (CO).

EXAMPLE 37

5-Fluoro-4-oxo-3-(3-phenoxybenzoylamino)-pentanoic Acid

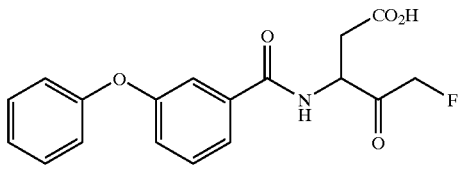

This was prepared using procedures similar to those described in Example 1 to give a off-white powder: IR (solid) 1643, 1744, 1782; $^1$H NMR (DMSO) δ 2.6–3.3 (2H, m), 4.4–4.6 (0.8H, m), 4.7–4.9 (1H, m), 5.1–5.4 (1.2H, m), 7.0 (2H, m), 7.1–7.2 (2H, m), 7.4–7.6 (4H, m), 7.6–7.7 (1H, m), 8.5–9.0 (1H, m); $^{13}$C NMR (DMSO) δ 32.82, 34.50, 34.60(CH$_2$), 52.58, 53.18(CH), 81.39, 81.87, 83.14, 83.57, 83.62, 85.35(CH$_2$), 117.82, 117.96, 119.04, 119.09, 119.15, 121.99, 122.18, 122.24, 122.84, 122.89, 124.11, 124.18, 130.46, 130.54(ArCH), 135.48, 135.96, 136.05 (ArC), 156.66, 156.79, 157.00, 157.10, 165.96, 166.11, 166.15, 172.06, 173.37, 174.41, 180.59, 202.86, 203.00 (CO).

EXAMPLE 38

5-Fluoro-3-(1-naphthylacetamido)-4-oxo-pentanoic Acid

This was prepared using procedures similar to those described in Example 1 to give a yellow gum: $^1$H NMR (DMSO) δ 2.59–2.90 (2H, m), 3.99 (2H, s), 4.27–4.48 (0.5H, m), 4.58–4.69 (1H, m), 5.13 (1.5H, m, J 46.9 Hz), 7.42–7.56 (4H, m), 7.82–7.84 (1H, m), 7.92–7.94 (1H, m), 8.03–8.08 (1H, m), 8.48, 8.78 (1H, 2×d, J 8.1, 7.3 Hz); $^{13}$C NMR (DMSO) δ 34.9 (CH$_2$), 39.5 (CH$_2$), 52.2 (CH), 84.2 (d, J 178.7 Hz, CH$_2$F), 124.4 (CH), 125.8 (CH), 126.0 (CH), 126.4 (CH), 127.6 (CH), 128.2 (CH), 128.7 (CH), 132.3 (CO), 132.6 (C), 133.7 (C), 171.1 (CO), 172.1 (CO), 202.8 (d, J 14.6 Hz, CO).

EXAMPLE 39

3-Benzoylamino-5-chloro-4-oxo-pentanoic Acid

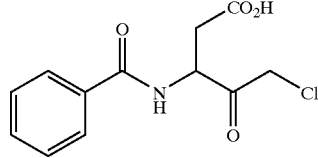

This was prepared from 3-benzoylamino-5-chloro-4-oxo-pentanoic acid tert-butyl ester using a procedure similar to that described in Method B to give colourless crystals: $^1$H NMR (DMSO) δ 2.68 (1H, dd), 2.90 (1H, dd), 3.85 (0.1H, m), 4.67 (0.9H, s), 4.90 (1H, m), 7.46 (2H, m), 7.55 (1H, m), 7.88 (2H, m), 88.99 (1H, d); $^{13}$C NMR (DMSO) 35.00 (CH$_2$), 48.21 (CH$_2$), 104.81, 127.81, 129.31, 132.09 (ArCH), 166.99 (CO), 172.68 (CO), 200.11 (CO).

Testing

Caspase-8 Assay

The assay for caspase-8 activity was based on the cleavage of a fluorogenic substrate by recombinant, purified human caspase-8 essentially according to the method described by Garcia-Calvo et al (1998) *J. Biol. Chem.* 273:32608–32613.

Materials

Assay Buffer: 10 mM Tris-HCl (Sigma T-3038), 1 mM dithiothreitol (DTT) (Calbiochem 233153), 0.1% CHAPS (Sigma C-3023), pH 7.5. Purified recombinant human Caspase-8. Substrate (acetyl-Asp-Glu-Val-Asp-amino-4-methyl coumarin, ACDEVD-AMC) (Bachem, I-1660). Serial dilution of test compound in DMSO (Sigma D-2650).

Method 70 microliters (μl) assay buffer, 20 μl of substrate and 5 μl of the inhibitor solution were added to the wells of a 96-well microtiter assay plate giving a final concentration of 1.5 nM caspase-8 and 10 μM substrate. The plate was incubated at 50° C. for 15 minutes in a thermostatically controlled plate warmer (Wesbart, UK). The reaction was then started by the addition of enzyme directly to the wells. The reaction was monitored continuously for 20 minutes in a fluorimeter (SPECTRAmax Gemini, Molecular Devices) at 37° C. by following the release of AMC fluorophor at an excitation wavelength of 390 nm and an emission wavelength of 460 nm. For each well, the observed rate of enzyme inactivation at a particular inhibitor concentration, $k_{obs}$, was computed by direct fits of the data to the equation derived by Thornberry et al., (1994, *Biochemistry* 33, 3943–3939) using a non-linear least squares analysis computer program (PRISM 2.0, Graph Pad Software). To obtain the second order rate constant, $k_{inact}$, $k_{obs}$ values were plotted against their respective inhibitor concentrations and $k_{inact}$ values were subsequently calculated by computerized linear regression.

Table 1 below shows inhibition of caspase-8 activity for selected compounds of this invention, as determined by the above method. The activity of each compound is rated according to its $K_{inact}$ (1/M/s) value. Compounds having a $k_{inact}$ (1/M/s) greater than 60,000 are rated "A", compounds having a $k_{inact}$ between 40,000 and 60,000 are rated "B" and compounds having a $k_{inact}$ less than 40,000 are rated "C".

TABLE 1

| Caspase-8 Activity | |
| --- | --- |
| Example No. | $K_{inact}$ (1/M/s) |
| 1 | A |
| 4 | C |
| 7 | B |
| 10 | B |
| 13 | C |
| 16 | B |
| 19 | B |
| 22 | B |
| 25 | B |
| 28 | C |
| 31 | C |
| 34 | A |
| 37 | A |

Caspase-9 Assay

Caspase-9 was purchased from Europa Bioproducts (order No UBC2088) and used with a concentration of 0.00125 units/ml (units defined by the manufacturer as amount of protease that cleaves 1 nmol of LEHD-pNA in 1 h at 37° C.). The assay was run as described for the caspase-8 assay except that the caspase-9 buffer additionally contained 8% glycerol (and the substrate concentration is 50 μM AcDEVD-AMC as opposed to 10 μM for caspase-8).

Table 2 below shows inhibition of caspase-9 activity for selected compounds of this invention, as determined by the above method. The activity of each compound was rated according to its $K_{inact}$ (1/M/s) value. Compounds having a $k_{inact}$ (1/M/s) greater than 60,000 are rated "A", compounds having a $k_{inact}$ less than 60,000 are rated "B".

TABLE 2

| Caspase-9 Activity | |
| --- | --- |
| Example No. | $K_{inact}$ (1/M/s) |
| 1 | A |
| 14 | B |
| 29 | B |

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 eg the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell-based assay to screen compounds for inhibition of the caspase-8-mediated apoptotic pathway.

Experimental Procedure

Jurkat E6.1 cells are cultured in complete medium consisting of RPMI-1640 (Sigma No)+10% foetal calf serum (Gibco BRL No.10099-141)+2 mM L-glutamine (Sigma No. G-7513). The cells are harvested in log phase of growth. 100 ml Cells at $5-8 \times 10^5$ cells/ml are transferred to sterile 50 ml Falcon centrifuge tubes and centrifuged for 5 minutes at $100 \times g$ at room temperature. The supernatant is removed and the combined cell pellets resuspended in 25 ml of complete medium. The cells are counted and the density adjusted to $2 \times 10^6$ cells/ml with complete medium.

The test compound was dissolved in dimethyl sulfoxide (DMSO)(Sigma No. D-2650) to give a 100 mM stock solution. This was diluted to 400 µM in complete medium, then serially diluted in a 96-well plate prior to addition to the cell assay plate.

100-µl of the cell suspension ($2 \times 10^6$ cells) were added to each well of a sterile 96-well round-bottomed cluster plate (Costar No. 3790). 50 µl of compound solution at the appropriate dilution and 50 µl of anti-Fas antibody, clone CH-11 (Kamiya No.MC-060) at a final concentration of 10 ng/ml, were added to the wells. Control wells were set up minus antibody and minus compound but with a serial dilution of DMSO as vehicle control. The plates were incubated for 16–18 hrs at 37° C. in 5% $CO_2$ and 95% humidity.

Apoptosis of the cells was measured by the quantitation of DNA fragmentation using a 'Cell Death Detection Assay' from Boehringer-Mannheim, No. 1544 675. After incubation for 16–18 hrs the assay plates were centrifuged at $100 \times g$ at room temperature for 5 minutes. 150 µl of the supernatant were removed and replaced by 150 µl of fresh complete medium. The cells were then harvested and 200 µl of the lysis buffer supplied in the assay kit were added to each well. The cells were triturated to ensure complete lysis and incubated for 30 minutes at 4° C. The plates were then centrifuged at $1900 \times g$ for 10 minutes and the supernatants diluted 1:20 in the incubation buffer provided. 100 µl of this solution were then assayed exactly according to the manufacturer's instructions supplied with the kit. $OD_{405}$ nm were measured 20 minutes after addition of the final substrate in a SPECTRAmax Plus plate reader (molecular Devices). $OD_{405}$ nm was plotted versus compound concentration and the $IC_{50}$ values for the compounds were calculated using the curve-fitting program SOFTmax Pro (Molecular Devices) using the four parameter fit option.

Table 3 below shows activity for selected compounds of this invention in the FAS induced apoptosis assay, as determined by the above method. The activity of each compound is rated according to its $IC_{50}$ (nM) value. Compounds having an $IC_{50}$ (nM) less than 200 are rated "A", compounds having an $IC_{50}$ between 200 and 1,000 are rated "B" and compounds having an $IC_{50}$ greater than 1,000 are rated "C".

TABLE 3

Activity in FAS Induced Apoptosis Assay

| Example No. | $IC_{50}$ (nM) |
|---|---|
| 1 | A |
| 4 | A |
| 7 | B |
| 10 | A |
| 13 | C |
| 16 | A |
| 19 | B |
| 22 | A |
| 25 | A |
| 28 | A |
| 31 | C |
| 34 | B |
| 37 | A |

While we have described a number of examples of this invention, it is apparent that these basic examples may be altered to provide other compounds of this invention. Therefore, it will be appreciated that the scope of this invention is to be defined by the appended claims rather than by the specific compounds that have been represented by way of example.

We claim:

1. A compound of formula I:

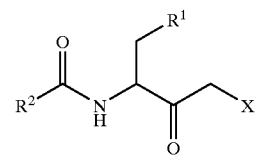

wherein X is F or Cl;

$R^1$ is COOH, COO(alkyl), or an isostere thereof; and $R^2$ is an aryl group.

2. The compound of claim 1, wherein: X is F.

3. The compound of claims 1 or 2, wherein: $R^1$ is COOH.

4. A pharmaceutical composition for treating or preventing caspase-mediated diseases comprising a pharmaceutically effective amount of a compound according to claims 1 and a pharmaceutically acceptable carrier.

5. A pharmaceutical composition comprising a compound according to claim 1 and a pharmaceutically acceptable carrier for treating complications associated with stroke, traumatic brain injury, spinal cord injury, meningitis, Alzheimer's disease, Parkinson's disease, Huntington's disease, Kennedy's disease, prion disease, multiple sclerosis, amyotrophic lateral sclerosis, spinal muscular atrophy, myocardial infarction, congestive heart failure and various other forms of acute and chronic heart disease, atherosclerosis, ageing, burns, organ transplant rejection, graft versus host disease, hepatitis-B, -C, G, various forms of liver disease including acute alcoholic hepatitis, yellow fever, dengue fever, Japanese encephalitis, glomerulonephritis, renal disease, H. pylori-associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves disease, autoimmune gastritis, autoimmune hemolytic anemia, autoimmune neutropenia, thrombocytopenia, HIV-related encephalitis, myasthenia gravis, small bowel ischemia in disease or post surgery, psoriasis, atopic dermatitis, myelodysplatic syndrome, acute and chronic myelogenous leukemia, metastatic melanoma, Kaposi's sarcoma, and Wiscott-Aldrich syndrome.

6. A pharmaceutical composition for inhibiting caspase activity comprising a pharmaceutically effective amount of a compound according to claim 1 and a pharmaceutically acceptable carrier.

7. A method for treating or preventing a caspase-mediated disease in a mammalian patient in need of such treatment comprising the step of administering to said patient an effective amount of a compound of formula I:

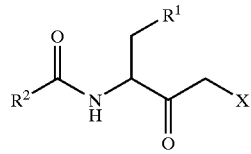

wherein X is F or Cl;

$R^1$ is COOH, COO(alkyl), or an isostere thereof; and $R^2$ is an aryl group.

8. The method of claim 7 wherein the compound has one or more of the following features: (a) X is F; (b) $R^1$ is COOH; and/or (c) $R^2$ is an optionally substituted group selected from phenyl, naphthyl, or a five, six, nine or ten membered heteroaryl having one or two heteroatoms.

9. The method of claim 8 wherein the compound has the following features: (a) X is F; (b) $R^1$ is COOH; and (c) $R^2$ is an optionally substituted group selected from phenyl, naphthyl, or a five, six, nine or ten membered heteroaryl having one or two heteroatoms.

10. The method of claim 7 wherein the caspase-mediated disease is selected from the group consisting of stroke, traumatic brain injury, spinal cord injury, meningitis, Alzheimers disease, Parkinson's disease, Huntington's disease, Kennedy's disease, prion disease, multiple sclerosis, amyotrophic lateral sclerosis, spinal muscular atrophy, myocardial infarction, congestive heart failure and various other forms of acute and chronic heart disease, atherosclerosis, ageing, burns, organ transplant rejection, graft versus host disease, hepatitis-B, -C, G, various forms of liver disease including acute alcoholic hepatitis, yellow fever, dengue fever, Japanese encephalitis, glomerulonephritis, renal disease, H. pylori-associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves disease, autoimmune gastritis, autoimmune hemolytic anemia, autoimmune neutropenia, thrombocytopenia, HIV-related encephalitis, myasthenia gravis, small bowel inchemia in disease or post surgery, psoriasis, atopic dermatitis, myelodysplatic syndrome, acute and chronic myelogenous leukemia, metastatic melanoma, Kaposi's sarcoma, and Wiscott-Aldrich syndrome.

11. A method for treating complications associated with coronary artery bypass grafts or a method of immunotherapy for the treatment of cancer in a mammalian patient in need of such treatment comprising the step of administering to said patient an effective amount of a compound of formula I:

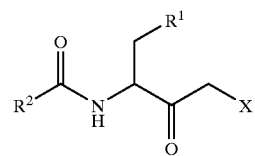

wherein X is F or Cl;

$R^1$ is COOH, COO(alkyl), or an isostere thereof; and $R^2$ is an aryl group.

12. The compound of claims 1 or 2, wherein: $R^2$ is an optionally substituted group selected from phenyl, naphthyl, or a five, six, nine or ten membered heteroaryl having one or two heteroatoms.

13. The compound of claim 12, wherein $R^1$ is COOH.

14. The compound according to claim 1, selected from the group consisting of:

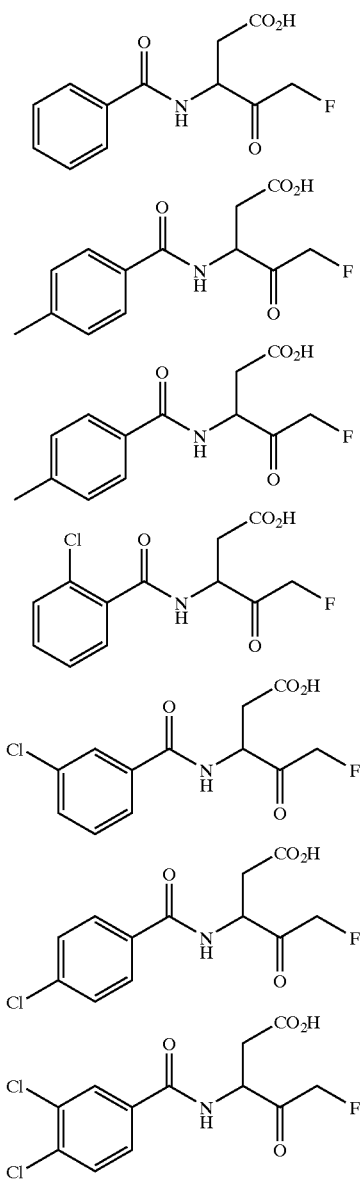

-continued
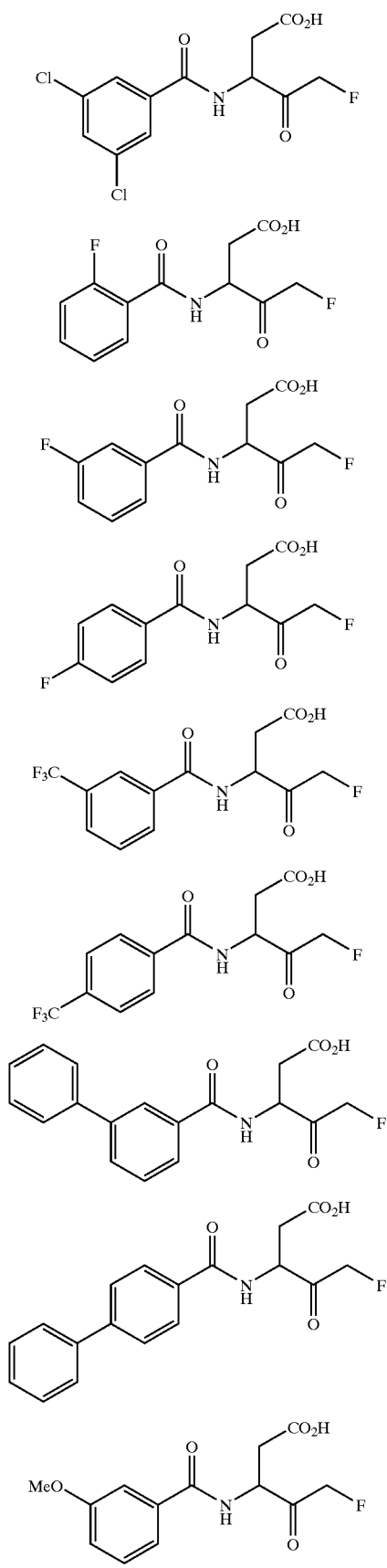
-continued
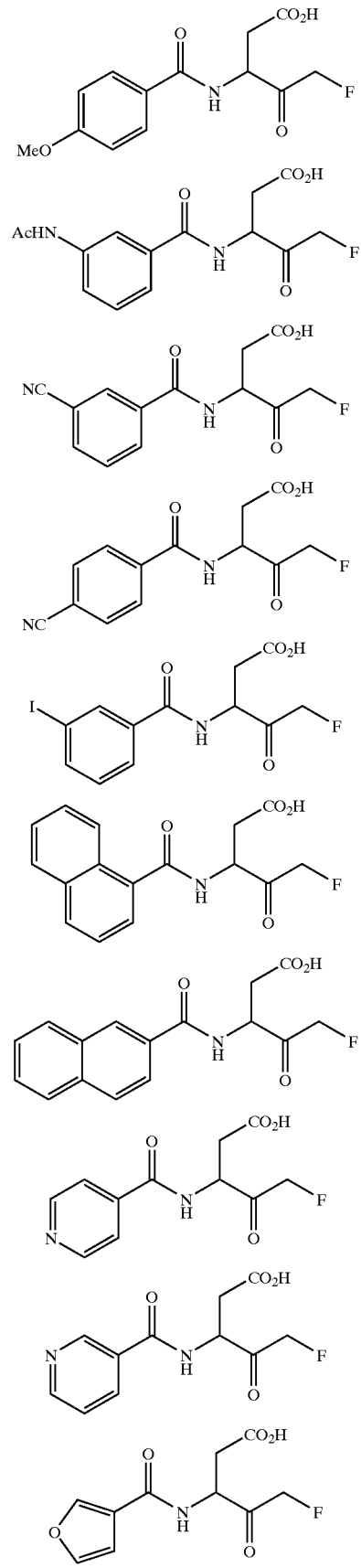

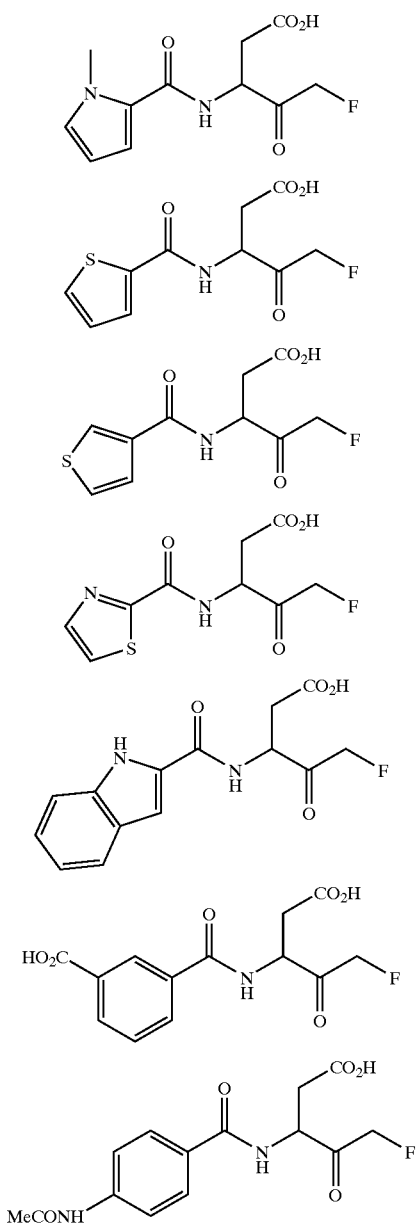
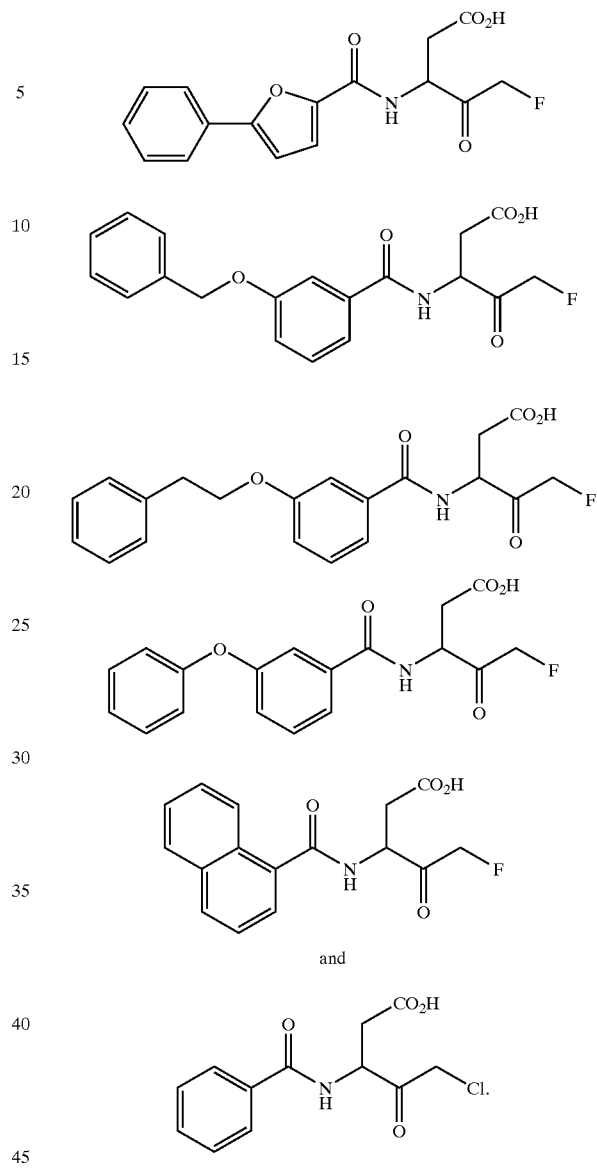
* * * * *